US012755464B2

(12) United States Patent
Ghodrati et al.

(10) Patent No.: US 12,755,464 B2
(45) Date of Patent: Oct. 6, 2026

(54) METHOD AND APPARATUS FOR ACCELERATED ACQUISITION AND RECONSTRUCTION OF CINE MRI USING A DEEP LEARNING BASED CONVOLUTIONAL NEURAL NETWORK

(71) Applicants: Siemens Healthineers AG, Forchheim (DE); The Regents of the University of California, Oakland, CA (US)

(72) Inventors: Vahid Ghodrati, Glendale, CA (US); Chang Gao, Los Angeles, CA (US); Peng Hu, Beverly Hills, CA (US); Xiaodong Zhong, Oak Park, CA (US); Jens Wetzl, Spardorf (DE); Jianing Pang, Seattle, WA (US)

(73) Assignees: Siemens Healthineers AG, Forchheim (DE); The Regents of the University of California, Oakland, CA (US)

( * ) Notice: Subject to any disclaimer, the term of this patent is extended or adjusted under 35 U.S.C. 154(b) by 611 days.

(21) Appl. No.: 17/814,877

(22) Filed: Jul. 26, 2022

(65) Prior Publication Data

US 2024/0037815 A1 Feb. 1, 2024

(51) Int. Cl.
*G06T 12/20* (2026.01)
*A61B 5/055* (2006.01)
(Continued)

(52) U.S. Cl.
CPC .............. *G06T 12/20* (2026.01); *A61B 5/055* (2013.01); *G01R 33/4818* (2013.01); *G06N 3/04* (2013.01);
(Continued)

(58) Field of Classification Search
CPC ..................... G06T 5/77; G06T 11/006; G06T 2207/30004; G06T 2207/20212;
(Continued)

(56) References Cited

U.S. PATENT DOCUMENTS 11,733,333 B2 * 8/2023 Koerzdoerfer ... G01R 33/56518 324/309
11,921,182 B2 * 3/2024 Zur ........................ G01R 33/50
(Continued)

OTHER PUBLICATIONS

Cheng J, Cui ZX, Huang W, Ke Z, Ying L, Wang H, Zhu Y, Liang D. Learning Data Consistency and its Application to Dynamic MR Imaging. IEEE Trans Med Imaging. Nov. 2021;40(11):3140-3153. doi: 10.1109/TMI.2021.3096232. Epub Oct. 27, 2021. PMID: 34252025. (Year: 2021).*

(Continued)

*Primary Examiner* — John Villecco
*Assistant Examiner* — Alexander John Rodgers

(57) ABSTRACT

Systems and methods for recreating images from undersampled MRI image data includes capturing undersampled MRI data and enhancing it with multiple cascading stages, each including a data consistency block in parallel to a convolutional neural network (CNN). The data consistency block adjusts each input image by a sensitivity map and performs hard replacement of acquired lines in k-space into the image. The CNN estimates a regularizer term that attempts to minimize a difference between a true image and the output of the data consistency block. At each stage, the output of CNN and data consistency block are added to create a set of output images that feed into the next stage.

16 Claims, 8 Drawing Sheets

(51) Int. Cl.

| | |
|---|---|
| ***G01R 33/48*** | (2006.01) |
| ***G06N 3/04*** | (2023.01) |
| ***G06N 3/08*** | (2023.01) |
| ***G06T 5/10*** | (2006.01) |
| ***G06T 5/50*** | (2006.01) |
| ***G06T 5/77*** | (2024.01) |

(52) U.S. Cl.
CPC ................. *G06N 3/08* (2013.01); *G06T 5/10* (2013.01); *G06T 5/50* (2013.01); *G06T 5/77* (2024.01); *G06T 2207/10088* (2013.01); *G06T 2207/20084* (2013.01); *G06T 2207/20212* (2013.01); *G06T 2207/30004* (2013.01); *G06T 2210/41* (2013.01)

(58) Field of Classification Search
CPC ....... G06T 2210/41; G06T 2207/20084; G06T 2207/10088; G06T 5/10; G06T 5/50; G06N 3/08; G06N 3/04; G01R 33/4818; A61B 5/055
See application file for complete search history.

(56) References Cited

U.S. PATENT DOCUMENTS

| | | | | |
|---|---|---|---|---|
| 12,315,047 | B2 * | 5/2025 | Arberet | G16H 30/40 |
| 2020/0103483 | A1 * | 4/2020 | Hardy | G01R 33/5608 |
| 2020/0311878 | A1 * | 10/2020 | Matsuura | G06F 18/2115 |
| 2020/0408864 | A1 * | 12/2020 | Mailhe | G06N 3/088 |
| 2021/0033688 | A1 * | 2/2021 | Koch | A61B 5/7267 |
| 2021/0150783 | A1 * | 5/2021 | Arberet | G06N 3/045 |
| 2022/0215600 | A1 * | 7/2022 | Arberet | G16H 30/40 |
| 2022/0252683 | A1 * | 8/2022 | Mostapha | G01R 33/246 |
| 2022/0343564 | A1 * | 10/2022 | Hosseini | G01R 33/5608 |
| 2022/0373630 | A1 * | 11/2022 | Dou | G06T 7/262 |
| 2023/0186532 | A1 * | 6/2023 | Schuelke | G01R 33/543<br>324/309 |

OTHER PUBLICATIONS

Gruber B, Froeling M, Leiner T, Klomp DWJ. RF coils: A practical guide for nonphysicists. J Magn Reson Imaging. Jun. 13, 2018; (Year: 2018).*

Nana R, Hu X. Data consistency criterion for selecting parameters for k-space-based reconstruction in parallel imaging. Magn Reson Imaging. Jan. 2010;28(1):119-28. doi: 10.1016/j.mri.2009.05.047. Epub Jun. 30, 2009. PMID: 19570636; PMCID: PMC2789867. (Year: 2009).*

Küstner, T., Fuin, N., Hammernik, K. et al. "CINENet: deep learning-based 3D cardiac Cine MRI reconstruction with multi-coil complex-valued 4D spatio-temporal convolutions" Sci Rep 10, 13710 (2020).

Sandino, CM, Lai, P, Vasanawala, SS, Cheng, JY. Accelerating cardiac cine MRI using a deep learning-based Espirit reconstruction. Magn Reson Med. 2020; 85: 152-167.

EP search report dated Dec. 18, 2023 in EP Application No. 23187250.8, 10 pages.

Menchón-Lara, Rosa-María, et al. "Reconstruction techniques for cardiac cine MRI." Insights into imaging 10 (2019): 1-16.

Kouzehkonan, Vahid Ghodrati. Deep Neural Networks for Cardiovascular Magnetic Resonance Imaging. University of California, Los Angeles, 2022.

* cited by examiner

METHOD AND APPARATUS FOR ACCELERATED ACQUISITION AND RECONSTRUCTION OF CINE MRI USING A DEEP LEARNING BASED CONVOLUTIONAL NEURAL NETWORK

BACKGROUND

Motion-sensitive magnetic resonance imaging (MRI), or cine-mode MRI can be used to observe fluid flow, such as cerebral spinal (CSF) or airway or ventricular motion or any other anatomy where detection of motion is useful. Software used by an MRI system can time images to a trigger signal, such as heartbeat or breathing to capture images that are phase shifted relative to the signal to capture cinematic frames that can highlight motion relative to that trigger. However, because successive images are not truly successive or time-adjacent, the way a video image can be captured with an image sensor, the relative quality of the animation created by cine MRI is less than ideal. Traditionally, multiple acquisitions are used to reduce artifacts, leading to a slow acquisition process to improve cine MRI quality.

SUMMARY

Described herein are systems and methods for reconstructing undersampled MRI images using a neural network. According to one embodiment, a system for recreating images from undersampled MRI image data includes an MRI imaging system comprising a plurality of magnets and RF coils configured to acquire undersampled MRI image data that include one or more images, each having a plurality of non-contiguous acquired scan lines and a processor and memory configured to execute software instructions that implement a series of cascading image enhancing stages that each produce enhanced output image data from input image data. A first stage receives the undersampled MRI image data while each remaining stage receives the output image data from a previous stage. Each stage includes a data consistency block that generates multi-coil input images by multiplying a sensitivity map, applies a first Fourier transform, replaces data in each image with the acquired scan lines at respective locations, and performs a second inverse Fourier transform. Each stage further includes a convolutional neural network (CNN) configured to estimate a regularizer term for the input image data, wherein the regularizer term attempts to minimize a difference between a true image and the output of the data consistency block. Each stage further includes a combinational block that combines the outputs of the data consistency block and CNN to create the output image data for the stage. The system further includes a memory configured to store recreated image data from a final stage of the cascading image enhancing stages.

According to one aspect of some embodiments, undersampled MRI image data includes a group of sequentially captured images of a patient. The sequentially captured images can be captured relative to a one of a patient's heartbeat and breathing. Each CNN in each stage can consider the group of sequentially captured images to create the regularizer term for each individual image. A location in k-space of the non-contiguous acquired scan lines can vary between subsequent images. According to one aspect of some embodiments, each CNN is a five-layer CNN. According to another aspect of some embodiments, the series of cascading image enhancing stages comprised eight stages. According to another aspect of some embodiments, the undersampled MRI image data is undersampled by a factor of at least 8×.

According to one embodiment, a method for recreating images from undersampled MRI image data includes receiving undersampled MRI image data that include one or more images, each having a plurality of non-contiguous acquired scan lines, and executing software instructions that implement a series of cascading image enhancing stages that together recreate images from the undersampled MRI image data, where each stage feeds an enhanced output image data to the next stage. The method further includes creating consistent data within each stage by adjusting the input image data by one of more sensitivity maps, applying a first Fourier transform, replacing data in each image with the acquired scan lines at respective locations, and performing a second Fourier transform. The method further includes estimating a regularizer term for the input image data within each stage using a convolutional neural network (CNN), wherein the regularizer term attempts to minimize a difference between a true image and the output of the data consistency block, and combining the outputs of the data consistency block and CNN to create the output image data for the stage. A recreated image data from a final stage of the cascading image enhancing stages is output.

FIGURES

The accompanying drawings, which are incorporated in and form a part of the specification, illustrate the embodiments of the invention and together with the written description explain the principles, characteristics, and features of the invention. In the drawings.

DESCRIPTION

Figure 1:
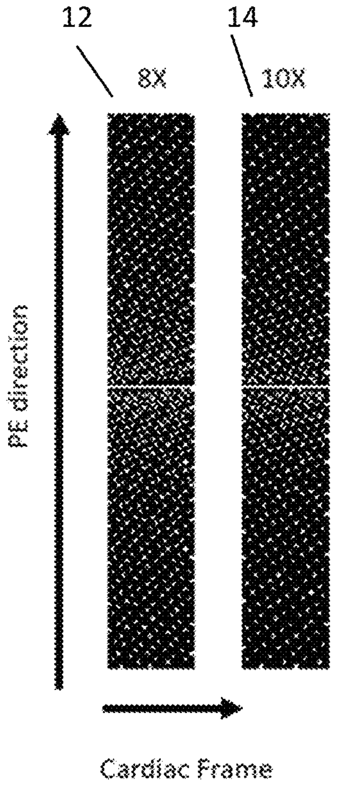
FIG. 1 is a diagram of exemplary undersampling masks for use with some embodiments.

This disclosure is not limited to the particular systems, devices and methods described, as these may vary. The terminology used in the description is for the purpose of describing the particular versions or embodiments only, and is not intended to limit the scope.

As used herein, the terms "algorithm," "system," "module," or "engine," if used herein, are not intended to be limiting of any particular implementation for accomplishing and/or performing the actions, steps, processes, etc., attributable to and/or performed thereby. An algorithm, system, module, and/or engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular algorithm, system, module, and/or engine is, unless otherwise specified, for purposes of convenience of reference and not intended to be limiting to a specific implementation. Additionally, any functionality attributed to an algorithm, system, module, and/or engine may be equally performed by multiple algorithms, systems, modules, and/or engines, incorporated into and/or combined with the functionality of another algorithm, system, module, and/or engine of the same or different type, or distributed across one or more algorithms, systems, modules, and/or engines of various configurations.

As used herein, the terms "MM sequence," "pulse sequence," or "MM pulse sequence" are interchangeable and can include a particular combination of pulse sequences and/or pulsed field gradients that result in a particular set of MRI data. An MRI sequence can be used either individually or in combination with one or more other MRI sequences (i.e., multi-parametric MRI).

As used herein, the term "MRI data" can include an MRI image or any other data obtained via MRI (e.g., biomarker data or a parameter map). An MRI image can include a three-dimensional image or a two-dimensional image (e.g., a slice of a three-dimensional image).

Embodiments use deep learning techniques, such as convolutional neural networks (CNNs) to accelerate the construction of dynamic MRI animations. Experiments using these embodiments reveal that artifact-corrected dynamic/cine MRI images can be acquired and reconstructed with 8x-10x undersampling, making these techniques more efficient than the prior art.

These techniques can be used for any temporally dynamic imaging, such as contrast-enhanced imaging. Cine MRI is one important application that can benefit from these techniques. Techniques utilize variable splitting to solve the optimization problems of dynamic MRI. In some embodiments, information is used from temporally adjacent frames to accelerate the solution.

Generally, in MRI imaging, an MRI signal is sampled repeatedly. Each iteration improves the image quality/detail. However, each iteration takes time, often requiring multiple seconds to acquire an image. Undersampling allows faster acquisition, but estimates need to be created to fill in the missing samples. The better the estimates of the missing information, the better undersampling techniques can be used. In various embodiments, machine learning is used to fill in missing information from undersampled images. Traditional techniques require relatively lots of time for this process. Time constraints are exacerbated in cine or dynamic imaging, making traditional approaches less desirable.

MRI images are often created using a rasterized approach, with phase encoding and frequency encoded directions. For a full image capture, each cartesian point in the phase and frequency direction is captured with the RF imaging coil. For an undersampled image, only certain phase encoding lines are captured (which includes each frequency encoding point along that sampled phase). In various embodiments of the techniques described herein, the specific phase line that is sampled varies with each subsequent image. In contrast, it is common to undersample the same phase lines when acquiring static images.

FIG. 1 shows an exemplary undersampling mask for 8x (12) and 10x (14) acceleration factors through the cardiac phases. Although FIG. 1 shows an example undersampling k-space mask with a single k-space center line and randomly sampled individual points, other undersampling k-space masks are also supported by the proposed network, including, but not limited to, a mask with zero k-space center line or k-space center lines more than 1, as well as sampled individual points following specific algorithms or patterns.

White points show the position of the phase encoding lines through subsequent frames. In each mask, the y-axis represents the location of sampled scanlines in the phase-encoding direction (where data is collected for all frequency encoding locations in that line) and the x-axis is a temporal axis, showing how scanlines change for each successive frame. In this example, successive frames can be triggered off a cardiac rhythm, allowing cine capture and animation of MRI images by shifting the phase of the image relative to the rhythm. Other trigger signals, such as breathing can also be used. In mask 12, one in eight lines are sampled, yielding 8x undersampling; in mask 14, one in ten lines are sampled, yielding 10x undersampling. A learning model can be applied to this undersampled data to fill in an approximation of the missing imaging data.

General Compressed Sensing Model: In general, the MR image reconstruction problem can be formulated as an inverse problem Fm=y, where m is the complex-valued image series formatted as an $N=N_m \times N_y \times N_t$ column vector, F is the Fourier encoding matrix, and y is the measurement k-space vector. Undersampling schemes are applied in practice to accelerate the acquisition process. Because of the applied undersampling, the inverse problem formulation would change to $F_u m=y_u$, where $F_u$ is a composite operator with size M×N includes sensitivity maps S, Fourier encoding matrix F, and binary undersampling mask U. In MR undersampled inverse problems, usually the number of measurements M is significantly less than the number of unknown N (M<<N). Thus, a direct solution is not possible because the underdetermined nature of the data allows for multiple image solutions. To solve this problem, two general approaches can be used: Parallel Imaging (PI), which relies on using channel information to turn the underdetermined set of equations into an overdetermined problem; and Compressed Sensing (CS), which takes advantage of the incoherent measurements along with appropriate regularizers to solve the underdetermined MR reconstruction problem. Embodiments focus on the second category, CS. Conventional CS algorithms estimate the reconstructed image x by minimizing the constrained optimization problem in the k-space. To solve for image m given undersampled k-space $y_i$, the compressed sensing reconstruction can be formulated as minimizing the following optimization problem:

$$\min_m \left\{ \frac{\lambda}{2} \sum_{i=1}^{n_c} \|\mathcal{D}\mathcal{F}S_i m - y_i\|_2^2 + \mathcal{R}(m) \right\} \quad \text{[Equation 1]}$$

In the data consistency/fidelity term (first term in Eq. 1), m is the estimated image, D is the undersampling mask/matrix, F is the Fourier transform, and S denotes the sensitivity map of the MRI RF receive coils ($S_i$ is the sensitivity of the $i^{th}$ channel coil). λ controls the weight of the data consistency term, and the number of channels is presented by nc. The regularization term (second term in Eq. 1) R(m) generally is a sparse regularizer, such as total-variation or the first norm of the wavelet transform of m.

There are two points about Equation 1 worth noting: 1) the regularizer term, R(m), is a fixed operation and has to be defined a priori; and 2) solving such an optimization problem requires an iterative algorithm which could lead to a long reconstruction time.

To optimize the above equation efficiently, variable splitting is used by decoupling m in the regularization from the data fidelity term and decomposition of $S_i$m such that no dense matrix inversion is involved in subsequent calculations. The problem becomes a multi-variable optimization problem:

$$\min_{m,u,x_i}\left\{\frac{\lambda}{2}\sum_{i=1}^{n_c}\|U\mathcal{F}x_i - y_i\|_2^2 + \mathcal{R}(u) + \frac{\alpha}{2}\sum_{i=1}^{n_c}\|x_i - S_i m\|_2^2 + \frac{\beta}{2}\sum_{i=1}^{n_c}\|u - m\|_2^2\right\} \quad \text{[Equation 2]}$$

where α and β are introduced penalty weights.

To solve for the above equation, one needs to alternatively optimize m, u and $x_i$:

$$\begin{cases} u^{k+1} = \text{denoiser}(m^k) & [eq.\ 3a] \\ x_i^{k+1} = \mathcal{F}^{-1}\left(\left(\lambda\mathcal{D}^T\mathcal{D} + \alpha I\right)^{-1}\left(\alpha\mathcal{F}S_i m^k + \lambda\mathcal{D}^T y_i\right)\right)\forall\ i \in \{1, 2, \ldots, n_c\} & [eq.\ 3b] \\ m^{k+1} = \left(\beta I + \alpha\sum_{i=1}^{n_c} S_i^H S_i\right)^{-1}\left(\beta u^{k+1} + \alpha\sum_{i=1}^{n_c} S_i^H x_i^{k+1}\right) & [eq.\ 3c] \end{cases}$$

Here $$S_i^H$$

is the conjugate transpose of $$S_i$$

and I is the identity matrix of size N by N.

In this step, we have turned the original problem into a denoising problem (denoted by denoiser) and two other equations, both of which have closed-form solutions that can be computed pointwise. Equation 3a corresponds to CNN block, equation 3b corresponds to the data consistency block, and equation 3 is the weighted sum block in the network.

To accelerate the reconstruction process and design a more powerful regularizer based on the historical data, embodiments use a CNN to resolve the regularizer term. Embodiments apply the CS reconstruction problem in Equation 1 into a 3D neural network/CNN to accelerate the reconstruction process and learn a more powerful spatio-temporal regularizer. This regularizer term is calculated to attempt to minimize a difference between a true image and the output of the data consistency term.

Figure 2:
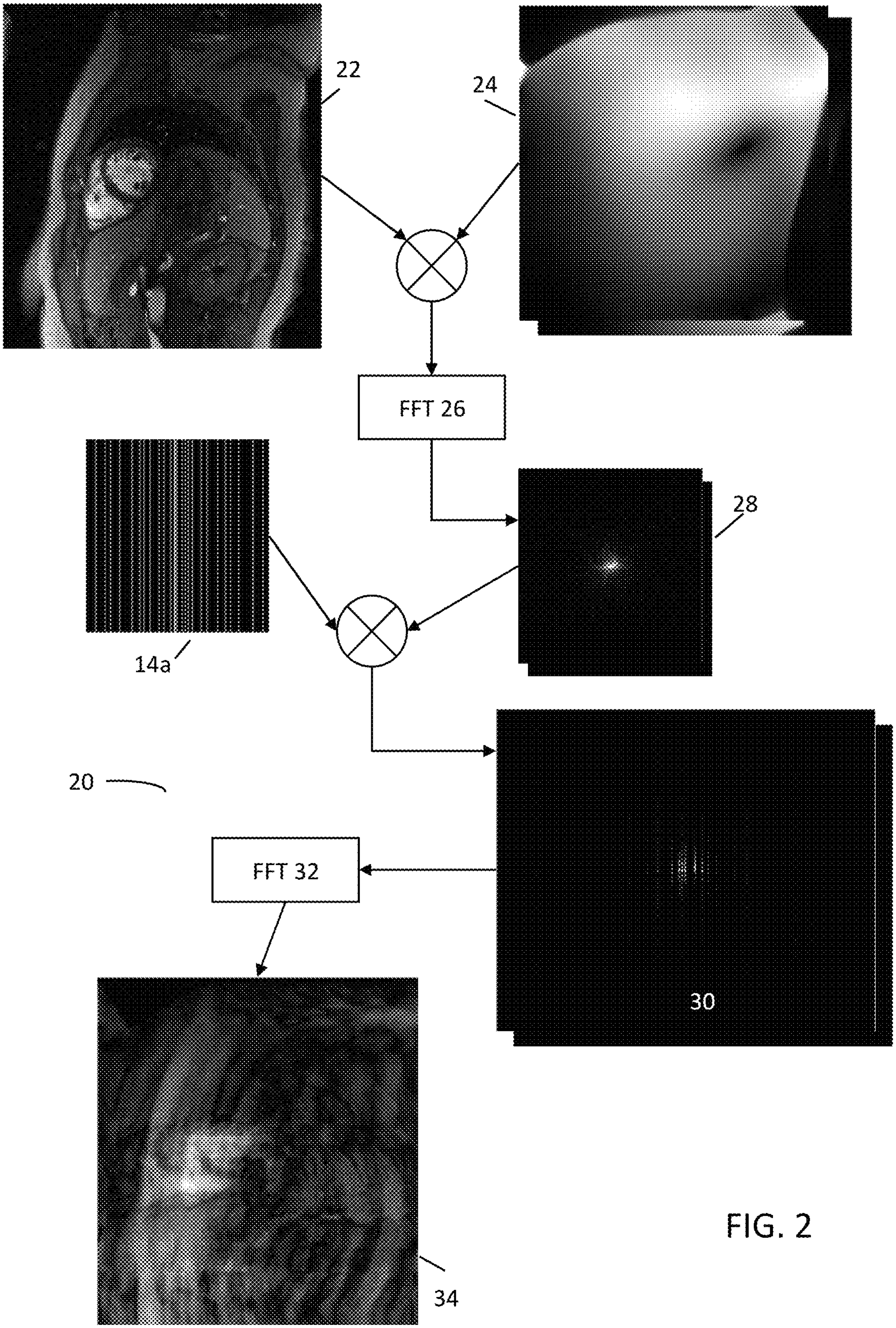
FIG. 2 is a dataflow diagram that illustrates how undersampling results in k-space information to be corrected by an estimation of a regularizer term for use with some embodiments.

FIG. 2 illustrates how undersampling results in missing k-space information which must be accurately estimated by a regularizer term, R(m). This process 20 can also be used to generate training images for some embodiments. An image 22 of patient anatomy can be affected by distortion that reflects an inhomogeneous sensitivity in the MRI receiver coils that captured the image. In this example, image 22 is a fully sampled image. An MRI system can be calibrated to create a sensitivity map 24, which reflects these intrinsic properties of the coils. Map 24 and image 22 can be multiplied to create multi-coil images that correspond to the acquired multi-coil k-space. The multi-coil images can be transformed into the k-space domain using a Fourier transform (such as a fast Fourier transform/FFT) 26, to create fully sampled k-space data 28.

To understand the effect of undersampling (or to generate training data for a CNN), a subsampling mask 14*a* can be multiplied by fully sampled k-space data 28, resulting in undersampled k-space data 30. As can be seen, the distribution of sampled lines in subsampling mask 14*a* need not be uniform and can benefit from denser sampling near the center of the k-space. When the undersampled k-space data 30 is transformed into the image domain via a Fourier transform, such as FFT 32, the resulting image 34 has artifacts from the undersampling. Various embodiments address the disparity between undersampled image 34 and fully sampled image 22 by using deep learning techniques to resolve an approximation of a regularizer term using time-adjacent images in dynamic imaging.

Figure 3:
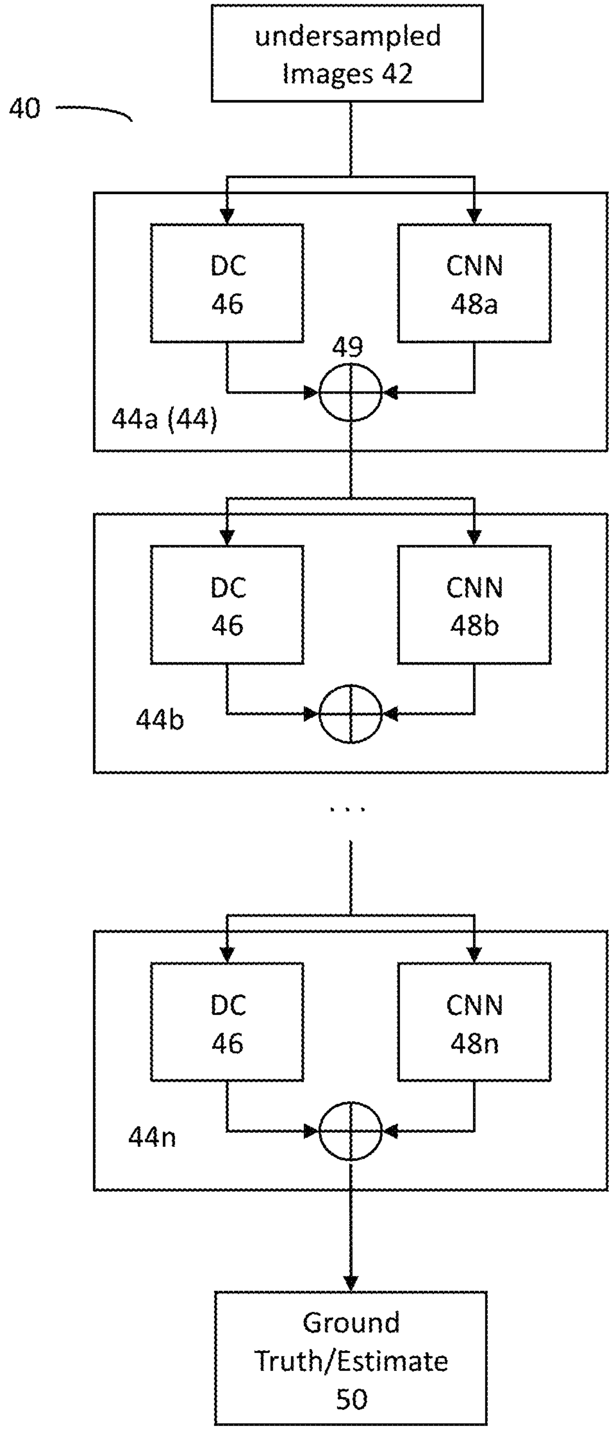
FIG. 3 is a software system diagram of the data flow for a deep learning system term for use with some embodiments.

FIG. 3 illustrates a system for recreating images from undersampled MRI image data using a deep learning system 40 for improving undersampled images 42. This can be implemented in any suitable processor and memory system. Deep learning system 40 includes a series of cascading image enhancing stages/convolutional stages 44 that each produce enhanced output image data from input image data, a first stage receiving the undersampled MRI image data while each remaining stage receives the output image data from a previous stage.

Undersampled images 42 include a series of undersampled dynamic/cine MRI images that progress temporally. In some embodiments, system 40 considers groups of images 42 together, rather than wholly individually. While the images change with time, the features largely relate frame-by-frame. This allows heavy under sampling, such as 8x or 10x as shown by experiments using some embodiments. Learning system 40 includes a sequentially cascading series of convolutional stages 44 (44*a*, 44*b*, 44*n* shown, where n is the total number of convolutional stages) forming an image reconstruction pipeline. In some embodiments, eight convolutional stages (n=8) are sufficient.

Each convolutional stage 44 includes two parallel blocks paralleling the terms of Equation 3: a data consistency block 46 that does not include a learning block; and a CNN block 48 (shown as 48*a-n*, as each CNN block arrives at different heuristic terms after training) that include a multi-layer convolutional neural network. A combinational block 49 adds the outputs of data consistency block 46 and CNN block 48 to create an enhanced output image set that is input to the next convolutional stage. These blocks are not intended to be means-plus-function elements, rather logical subsections of the algorithm for image reconstruction corresponding to the functional terms of Equation 1. An exemplary CNN has five layers, each with 64 nodes. Any conventional CNN algorithm can be used. The purpose of each CNN block is to learn and create a regularizer term to improve the estimated image at each convolutional stage to arrive estimated images stored in memory 50, which are close to ground truth. At each stage, the output of the data consistency block is combined with the regularizer term from the CNN. The resulting image is then fed into the next block until n blocks have iteratively improved the image.

System 40 and the relevant block are implements as software instructions in memory coupled to one or more processors, using any suitable computational hardware.

Figure 4:
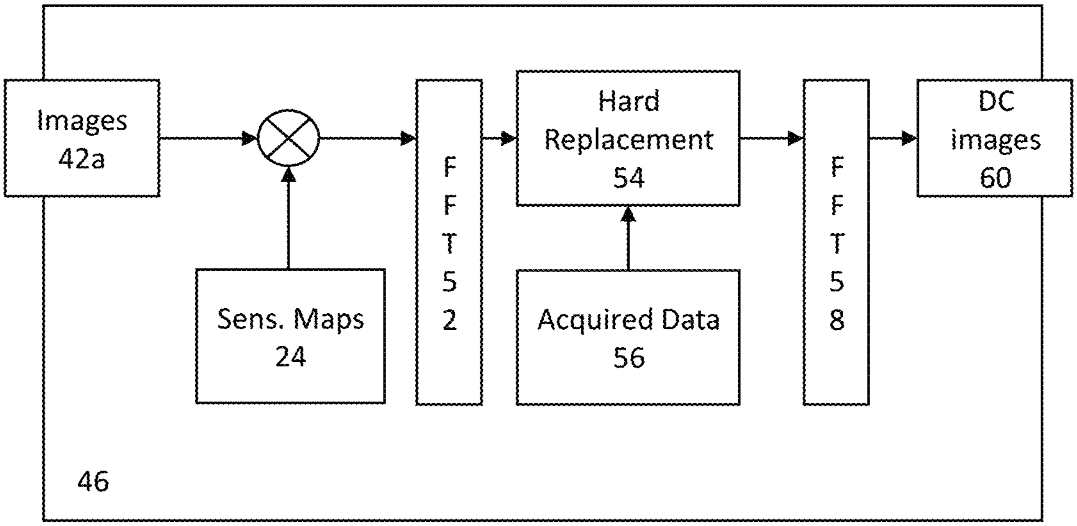
FIG. 4 is a software system diagram of an exemplary data consistency block for use with some embodiments.

FIG. 4 illustrates the details of an exemplary data consistency block 46. In each stage, the input images 42 or image estimation (42*a*, collectively) from the previous convolutional stage 44 are multiplied by the coil sensitivity map intrinsic to the MRI machine. The multi-coil images are then converted to the k-space domain using FFT 52. Once the data is in the k-space, data consistency is enforced by performing a hard replacement of the estimated data by replacing the portion of k-space data that corresponds to the undersampling mask with the actual acquired k-space data corresponding to the undersampling mask. That is, at each convolutional stage, in the data consistency block, known sampled data is replaced into the image data, ensuring that the k-space image estimate does not drift from the known correct MRI data as the image estimate evolves at each stage. Once k-space data has been corrected to match the acquired data for phase encoding lines that we sampled, the k-space data is transformed to the image domain using inverse FFT 58. This results in data-consistent images 60. Each data-consistent image includes known-sampled MRI data and therefore represents a possible solution of the image based on subsampled data.

Figure 5:
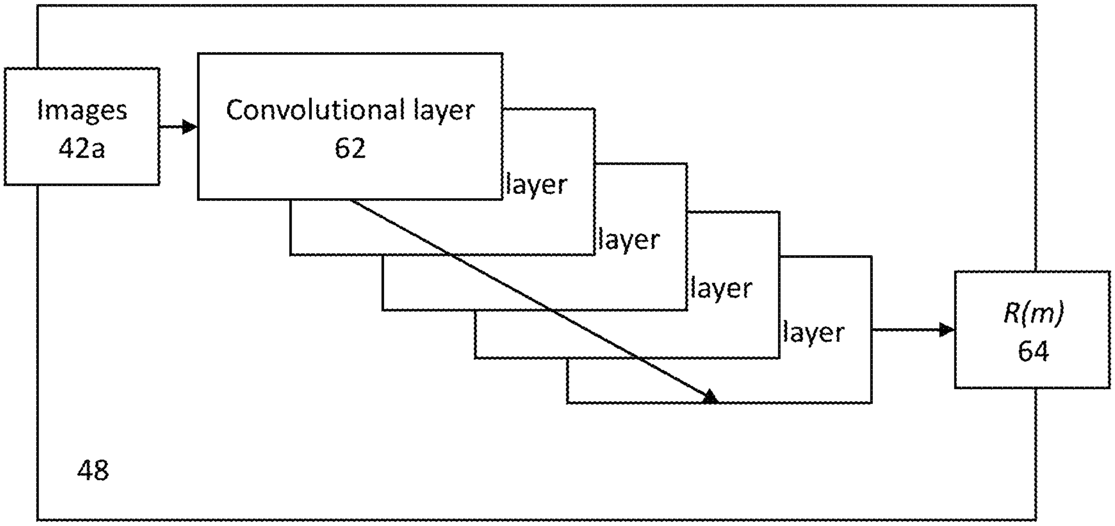
FIG. 5 is a software system diagram of an exemplary convolutional network or use with some embodiments.

FIG. 5 illustrates the 3D convolutional network in CNN block 48. Images are passed into a multi-layer CNN network including a plurality of convolutional layers 62, to arrive at an estimate of the regularizer term R(m) 64 that approximates the error of the output from each data consistency block. In some embodiments, five convolutional layers having 64 nodes are used, but any suitable number and size of layers can be used. This was found empirically to provide a good trade-off of accuracy and speed without overfitting the model to the training set. The resulting R(m) model 64 from the CNN block 48 is then added to the data consistency images 60 from the data consistency block 46 to arrive at an estimated image for each convolutional stage. After several stages, the estimated image 50 should approximate ground truth.

Data Preparation and Training:

The embodiment illustrated in FIGS. 3-5 was implemented in software and tested with good results. To train and evaluate the network, the experiment used retrospectively acquired clinical breath-held 2D multi-slice, ECG-triggered, GRAPPA 2X, bSSFP cardiac cine MR images in the short-axis, horizontal long-axis, and vertical long-axis views from 42 patients. The experiment divided this data into 25 patients' data (583 dynamic images) to train the network and 17 patient cases (272 dynamic images) for testing the network. Since the retrospectively acquired data was based on the GRAPPA 2X, a proper ICE function was employed to reconstruct the free of the aliasing single-channel complex image for the data. A particular ICE function was used to extract the sensitivity maps for each dynamic set of images. The main reason behind using the ICE function to calculate the sensitivity maps was training the data on more realistic images, thus improving the performance of the network and its compatibility with the Siemens scanner.

For training the network, five sets of data including sensitivity maps, multi-channel undersampled raw data (k-space), undersampling masks (binary masks), coil combined single-channel complex zero-filled dynamic images, and coil combined single-channel complex aliasing free dynamic images (target) are required. FIG. 2 graphically summarized the required data for training the network. For the sake of clarity, data preparation was shown in FIG. 2 for a single image; for dynamic images, data from different frames were concatenated to a 3D matrix and processed using the same pipeline. Coil combination was achieved by summing up the images in an element-wise manner in the channel dimension. This multi-channel process is illustrated as a single image channel in FIG. 2.

For testing the network, only four sets of the data are required, including sensitivity maps, multi-channel undersampled raw data (k-space), undersampling masks (binary masks), and coil combined single-channel complex zero-filled dynamic images. Three points are considered in designing the undersampling mask: 1) initial sampling lines on (discretized) golden steps were calculated; 2) the initial calculated lines were repositioned based on a predefined density distribution; and 3) lines were sorted in a way that they zigzag across time to minimize the gradient jump.

For training the network, the Adam optimizer was used with the momentum parameter $\beta=0.9$, mini-batch size=1, and an initial learning rate of 0.0001 to minimize the L1 norm between the reconstructed dynamic images and the corresponding dynamic targets. Weights for the network were initiated with random normal distributions with a variance of $\sigma=0.01$ and mean$\mu=0$. The network was trained for five epochs, i.e., 5×8750 iterations in an end-to-end fashion based on the five sequential cardiac frames extracted from the dynamic training data. The training was performed with the Pytorch interface on a commercially available graphics processing unit (GPU) (NVIDIA Titan RTX, 24 GB RAM). Once the network was trained, it was tested based on the full-sized dynamic images rather than five sequential dynamic frames.

Figure 6:
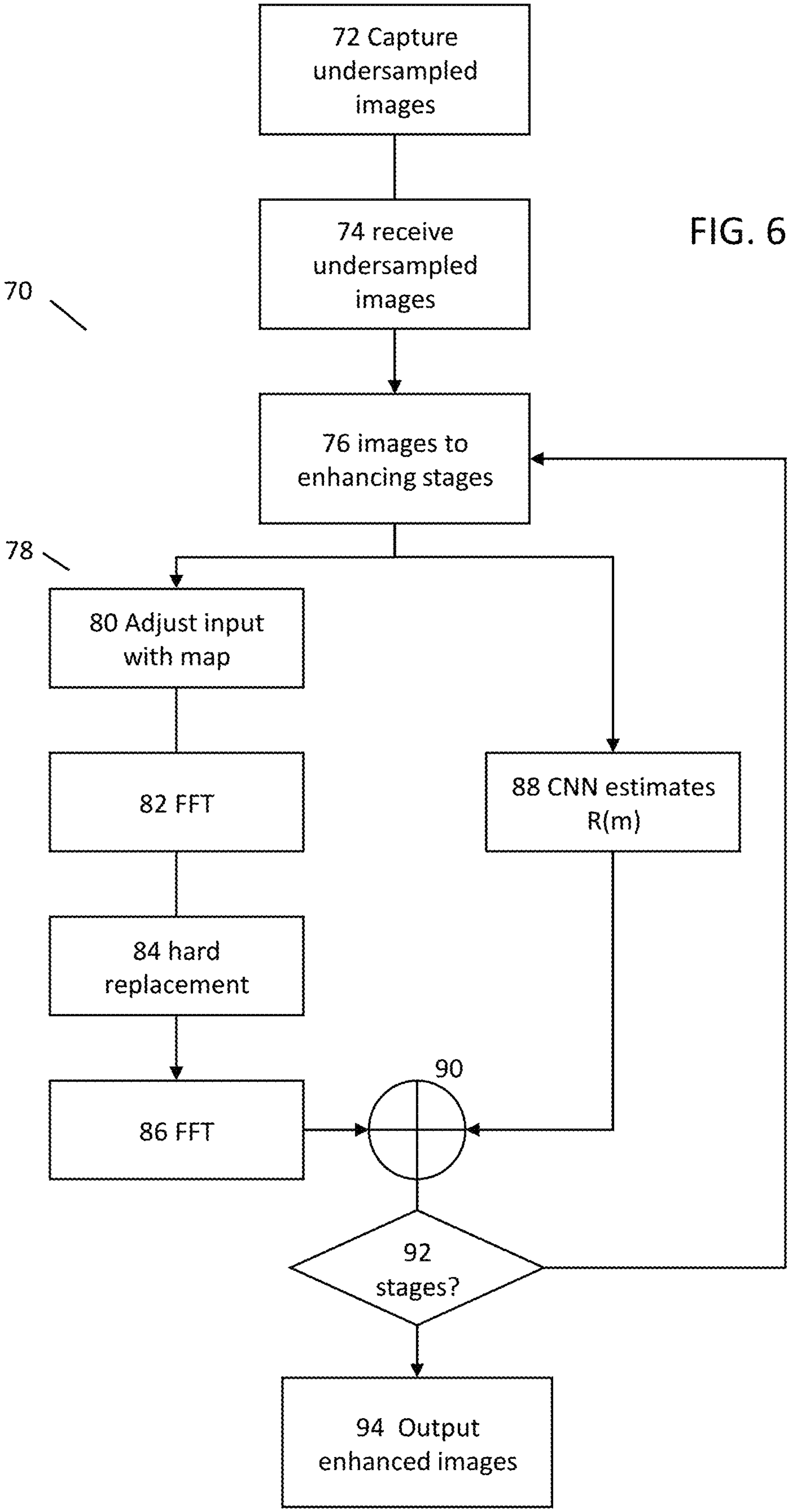
FIG. 6 is a flowchart of an exemplary method for reconstructing undersampled images in accordance with some embodiments.

FIG. 6 is a flowchart of an exemplary method 70 for reconstructing undersampled dynamic images in accordance with some embodiments. At step 72, an MRI system captures a series of dynamic images (such as cine images) using a suitable conventional MRI imaging technique. To speed up acquisition, these images are undersampled in accordance with the sampling strategy in accordance an undersampling mask that reduces the amount of data and acquisition time by some suitable large amount (such as reducing the number of phase encoding scan lines that are acquired by 8-10x vs. a full image capture.) The undersampling mask can vary in a predetermined manner between sequential images, as shown in FIG. 1. This undersampled data include one or more images, each having a plurality of non-contiguous acquired scan lines. For example, in dynamic/cine imaging, several sequential images are taken (often triggered by phase relative to a biological signal, such as heartbeat or breathing), each with a different mask for each image.

At step 74, a processor that implements the trained CNN stages receives the undersampled MRI image data from the MRI imaging system. Once the processor receives the image(s), images can be run through the multi-stage CNN system explained in FIG. 3, passing data in a cascading manner to image enhancing stages that are implemented at step 76. This includes data consistency steps 78 in parallel with CNN step 88. Each stage has a unique CNN and feeds the output from one stage into the input of the next, cascading an iteratively enhanced image set until the final stage outputs the finalized, recreated images from the undersampled image data that are substantially predictive of a fully sampled image.

Data consistency steps 78 include adjusting the input image received at each stage (e.g., by multiplying) using a sensitivity map of the MRI imaging system, at step 80. At step 82, an FFT is performed to bring the adjusted image into the k-space domain. At step 84, hard replacement of the resulting k-space data is performed, such that any lines in k-space that have been sampled and received at steps 74 and 72 are replaced with the actual lines of acquired undersampled data. This is because the predicted image for the fully sampled data should include the actual acquired lines be an accurate image. This prevents image drift as the stages progress. At step 86, once the k-space has been corrected to include the actual known data, a second FFT is performed to bring the data back to the image domain to create a data-consistent image set from the images input to the block, At parallel step 88, the processor estimates a regularizer term for the image data input to each stage using a CNN. The regularizer term attempts to minimize a difference between a true image and the output of the data consistency block. In some embodiments, the CNN is a 5-layer CNN. In some embodiments, the CNN layers consider multiple under-sampled, sequentially captured images as input for the recreation of a regularizer term for a single image.

At step 90, the processor, at each stage, combines the outputs of the data consistency block (78) and CNN (88) to create the output image data for the stage. At step 92, if there are any remained stages in the cascading pipeline, the resulting image data is passed to the next stage, where that stage implements steps 78-90 (using a CNN that has been uniquely trained for each stage for step 88). In some embodiments, there are eight stages used. Once there are no remaining stages, the processor stores and outputs a recreated image data from a final stage of the cascading image enhancing stages, at step 94. This image data includes a series of predicted fully sampled dynamic images from the undersampled data received at step 74.

Figure 7:
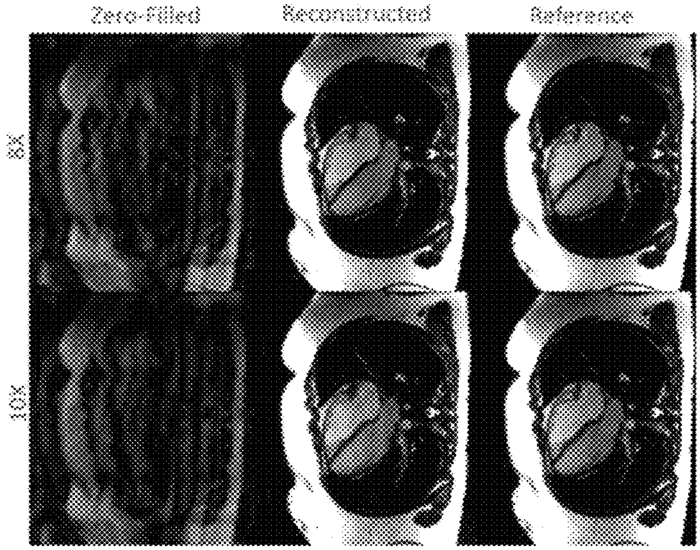
FIGS. 7 and 8 are examples of images reconstructed using 8X and 10X acceleration factors in accordance with some embodiments.
Figure 8:
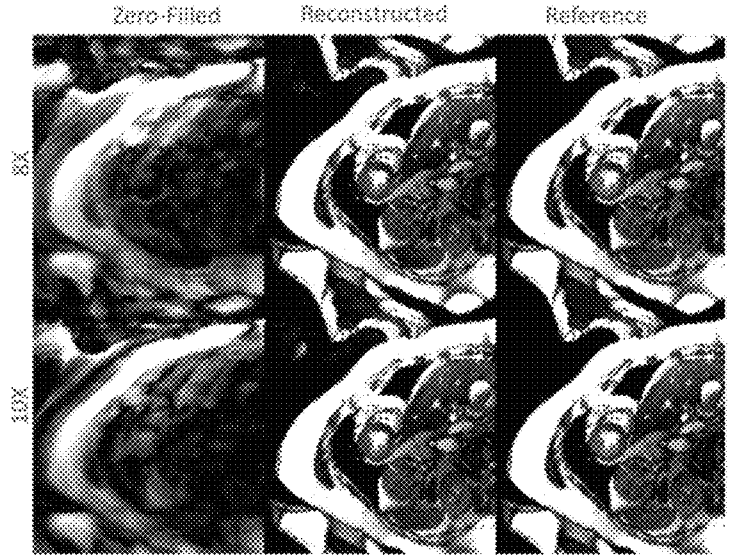

FIGS. 7 and 8 present example images with 8X and 10X acceleration factors. FIG. 7 shows the reconstruction results for the horizontal long axis (HLA) view of the cardiac image. This reveals the results of the system of FIG. 3 using arbitrarily selected test data for the HLA cardiac view for 8X and 10X acceleration factors. FIG. 8 shows the Qualitative reconstruction results of arbitrarily selected test data for the short-axis (SAX) cardiac view for 8X and 10X acceleration factors. Thus, experimental reconstruction results show that 8x and 10x subsampling acceleration can be handled using a CNN approach provide high-quality dynamic/cine imaging.

Figure 9A:
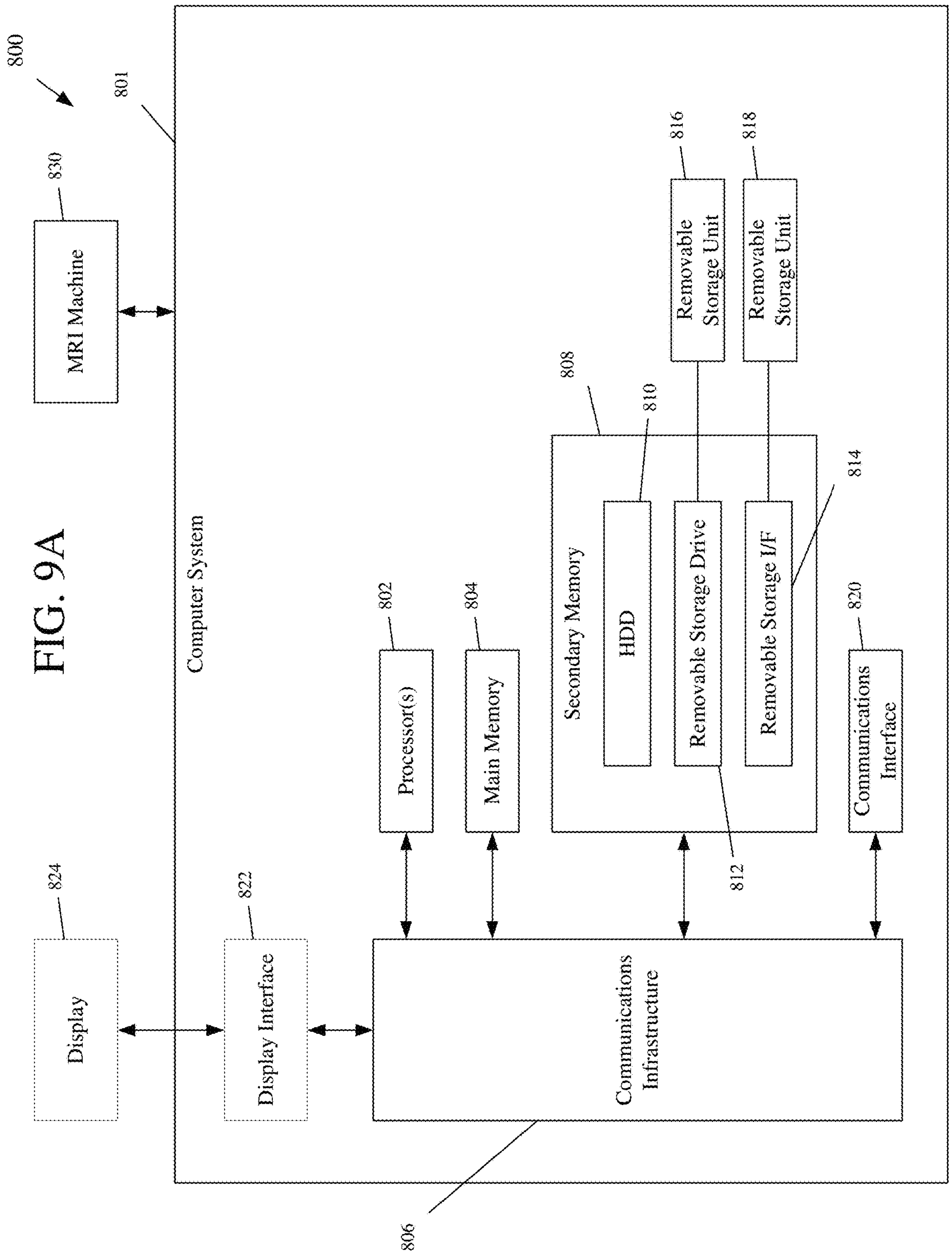
FIGS. 9A and 9B are system diagrams of an exemplary MRI and processor system suitable for implementing some embodiments.
Figure 9B:
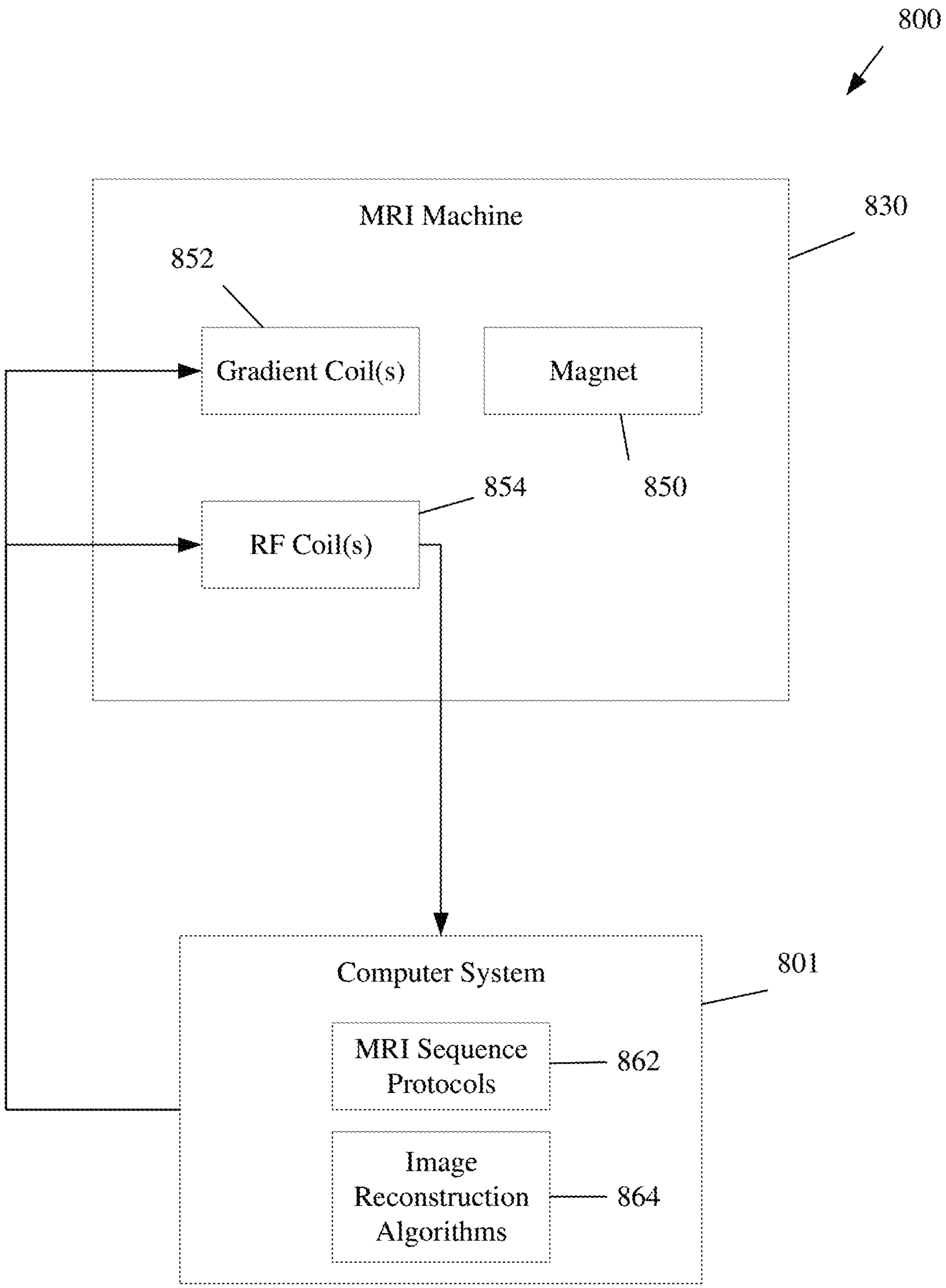

Medical Imaging System Architecture:

In some embodiments, the systems and techniques described above can be implemented in or by a medical imaging system, such as the medical imaging system 800 illustrated in FIGS. 9A and 9B.

FIG. 9A is an architecture diagram of medical imaging system 800 that may be used in some embodiments. As noted above, the medical imaging system 800 can include a computer system 801 and an imaging machine 830 (e.g., an MRI machine). The computer system 801 may include one or more processors 802. Each processor 802 is connected to a communication infrastructure 806 (e.g., a communications bus, cross-over bar, or network). The processor(s) 802 can include a CPU, a GPU, an AI accelerator, and/or a variety of other processor types. Computer system 801 may include a display interface 822 that forwards graphics, text, and other data from the communication infrastructure 806 (or from a frame buffer, not shown) for display on the display unit 824.

Computer system 801 may also include a main memory 804, such as a random access memory (RAM), and a secondary memory 808. The secondary memory 808 may include, for example, a hard disk drive (HDD) 810 and/or removable storage drive 812, which may represent a floppy disk drive, a magnetic tape drive, an optical disk drive, a memory stick, or the like as is known in the art. The removable storage drive 812 reads from and/or writes to a removable storage unit 816. Removable storage unit 816 may be a floppy disk, magnetic tape, optical disk, or the like. As will be understood, the removable storage unit 816 may include a computer readable storage medium having tangibly stored therein (embodied thereon) data and/or computer software instructions, e.g., for causing the processor(s) to perform various operations.

In alternative embodiments, secondary memory 808 may include other similar devices for allowing computer programs or other instructions to be loaded into computer system 801. Secondary memory 808 may include a removable storage unit 818 and a corresponding removable storage interface 814, which may be similar to removable storage drive 812, with its own removable storage unit 816. Examples of such removable storage units include, but are not limited to, USB or flash drives, which allow software and data to be transferred from the removable storage unit 816, 818 to computer system 801.

Computer system 801 may also include a communications interface 820. Communications interface 820 allows software and data to be transferred between computer system 801 and external devices. Examples of communications interface 820 may include a modem, Ethernet card, wireless network card, a Personal Computer Memory Card International Association (PCMCIA) slot and card, or the like. Software and data transferred via communications interface 820 may be in the form of signals, which may be electronic, electromagnetic, optical, or the like that are capable of being received by communications interface 820. These signals may be provided to communications interface 820 via a communications path (e.g., channel), which may be implemented using wire, cable, fiber optics, a telephone line, a cellular link, a radio frequency (RF) link and other communication channels.

In this document, the terms "computer program medium" and "non-transitory computer-readable storage medium" refer to media such as, but not limited to, media at removable storage drive 812, a hard disk installed in hard disk drive 810, or removable storage unit 816. These computer program products provide software to computer system 801. Computer programs (also referred to as computer control logic) may be stored in main memory 804 and/or secondary memory 808. Computer programs may also be received via communications interface 820. Such computer programs, when executed by a processor, enable the computer system 801 to perform the features of the methods discussed herein. For example, main memory 804, secondary memory 808, or removable storage units 816 or 818 may be encoded with computer program code (instructions) for performing operations corresponding to various processes disclosed herein.

Referring now to FIG. 9B, the MRI machine 830 can include a magnet 850 extending along a bore that is configured to receive a patient therein and that is configured to produce a generally uniform magnetic field, one or more gradient coils 852 that are configured to produce magnetic field gradients (e.g., linear gradients), and one or more RF coils 854 that are configured to transmit to RF signals to the patient's body and/or receive RF signals therefrom. The computer system 801 (embodiments of which are described in greater detail above) can store and implement calibration scan protocols 860, MRI sequences protocols 862, and/or image reconstruction algorithms 864, as well as a variety of other software modules known in the technical field. The MRI sequence protocols 862 can be embodied as instructions that, when executed by the computer system 801, cause the computer system 801 to control the gradient coils 852 and/or RF coils 854 to apply a particular sequence of magnetic field gradients and/or RF pulses to the patient. The image reconstruction algorithms 864 can be embodied as instructions that, when executed by the computer system 801, cause the computer system 801 to reconstruct an image of the patient based on the RF signal received from the patient (e.g., by the RF coils 854) as caused by the MRI sequence applied thereto. In one embodiment, the image reconstruction algorithms 864 could include a cascaded CNN trained using the techniques described above to remove or reduce image artifacts from an undersampled MR image.

It is understood by those familiar with the art that the system described herein may be implemented in hardware, firmware, or software encoded (e.g., as instructions executable by a processor) on a non-transitory computer-readable storage medium.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

Aspects of the present technical solutions are described herein with reference to flowchart illustrations and/or block diagrams of methods, apparatuses (systems), and computer program products according to embodiments of the technical solutions. It will be understood that each block of the flowchart illustrations and/or block diagrams, and combinations of blocks in the flowchart illustrations and/or block diagrams, can be implemented by computer readable program instructions.

These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions can also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present technical solutions. In this regard, each block in the flowchart or block diagrams can represent a module, segment, or portion of instructions, which includes one or more executable instructions for implementing the specified logical function(s). In some alternative implementations, the functions noted in the blocks can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A second action can be said to be "in response to" a first action independent of whether the second action results directly or indirectly from the first action. The second action can occur at a substantially later time than the first action and still be in response to the first action. Similarly, the second action can be said to be in response to the first action even if intervening actions take place between the first action and the second action, and even if one or more of the intervening actions directly cause the second action to be performed. For example, a second action can be in response to a first action if the first action sets a flag and a third action later initiates the second action whenever the flag is set.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

As used in this document, the singular forms "a," "an," and "the" include plural references unless the context clearly dictates otherwise. Unless defined otherwise, all technical and scientific terms used herein have the same meanings as commonly understood by one of ordinary skill in the art.

Nothing in this disclosure is to be construed as an admission that the embodiments described in this disclosure are not entitled to antedate such disclosure by virtue of prior invention.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 components refers to groups having 1, 2, or 3 components. Similarly, a group having 1-5 components refers to groups having 1, 2, 3, 4, or 5 components, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A system for recreating images from undersampled MRI image data comprising:

an MRI imaging system comprising a plurality of magnets and RF coils configured to acquire undersampled MRI image data that include one or more images, each having a plurality of non-contiguous acquired scan lines;

a processor and memory configured to execute software instructions that implement a series of cascading image enhancing stages that each produce enhanced output image data from input image data, a first stage receiving the undersampled MRI image data while each remaining stage receives the enhanced output image data from a previous stage, each stage including, a data consistency block configured to receive the enhanced output image data from the previous stage and generate multi-coil input images based on multiplying a sensitivity map by the enhanced output image data received from the previous stage, apply a first Fourier transform to convert the multi-coil input images to k-space data in a k-space domain, replace data in each image of the k-space data with the plurality of non-contiguous acquired scan lines at respective locations of each image of the k-space data, perform a second inverse Fourier transform to convert the k-space data to data-consistent images in an image domain, and output the data-consistent images including the plurality of non-contiguous acquired scan lines, a convolutional neural network (CNN) configured to estimate a regularizer term for the input image data, wherein the regularizer term is configured to minimize a difference between a true image and the output of the data consistency block, and a combinational block configured to combine the outputs of the data consistency block and CNN to create the enhanced output image data for the stage; and a memory configured to store recreated image data from a final stage of the cascading image enhancing stages.

2. The system of claim 1, wherein the undersampled MRI image data comprises a group of sequentially captured images of a patient.

3. The system of claim 2, wherein the sequentially captured images are captured relative to a one of a patient's heartbeat and breathing.

4. The system of claim 2, wherein each CNN in each stage considers the group of sequentially captured images to create the regularizer term for each individual image.

5. The system of claim 2, wherein a location in the k-space domain of the plurality of non-contiguous acquired scan lines varies between subsequent images.

6. The system of claim 1, wherein each CNN is a five-layer CNN.

7. The system of claim 1, wherein the series of cascading image enhancing stages comprised eight stages.

8. The system of claim 1, wherein the undersampled MRI image data is undersampled by a factor of at least 8x.

9. A method for recreating images from undersampled MRI image data comprising:

receiving undersampled MRI image data that include one or more images, each having a plurality of non-contiguous acquired scan lines;

executing software instructions that implement a series of cascading image enhancing stages that together recreate images from the undersampled MRI image data, each stage feeding an enhanced output image data to a next stage;

creating consistent data within each stage by receiving the enhanced output image data from a previous stage, adjusting input image data by one or more sensitivity maps based on multiplying the one or more sensitivity maps by the enhanced output image data received from the previous stage, applying a first Fourier transform to convert the input image data to k-space data in a k-space domain, replacing data in each image of the k-space data with the plurality of non-contiguous acquired scan lines at respective locations of each image of the k-space data, and performing a second Fourier transform to convert the k-space data to data-consistent images in an image domain, the data-consistent images including the plurality of non-contiguous acquired scan lines;

estimating a regularizer term for the input image data within each stage using a convolutional neural network (CNN), wherein the regularizer term is configured to minimize a difference between a true image and an output of a data consistency block;

combining the outputs of the data consistency block and CNN to create the enhanced output image data for the stage; and outputting a recreated image data from a final stage of the cascading image enhancing stages.

10. The method of claim 9, wherein the undersampled MRI image data comprises a group of sequentially captured images of a patient.

11. The method of claim 10, wherein the sequentially captured images are captured relative to a one of a patient's heartbeat and breathing.

12. The method of claim 10, wherein the step of estimating a regularizer term comprises considering the group of sequentially captured images to create the regularizer term for each individual image.

13. The method of claim 10, wherein a location in the k-space domain of the plurality of non-contiguous acquired scan lines varies between subsequent images.

14. The method of claim 9, wherein each CNN is a five-layer CNN.

15. The method of claim 9, wherein the series of cascading image enhancing stages comprised eight stages.

16. The method of claim 9, wherein the undersampled MRI image data is undersampled by a factor of at least 8x.

* * * * *